United States Patent [19]
Yelvington

[11] Patent Number: 5,866,085
[45] Date of Patent: Feb. 2, 1999

[54] DEVICE FOR THE ENCAPSULATION OF PLASTIC SYRINGES

[75] Inventor: Richard Yelvington, Jacksonville, Fla.

[73] Assignee: Imagination Medical, Inc., Jacksonville, Fla.

[21] Appl. No.: 858,284

[22] Filed: May 19, 1997

[51] Int. Cl.[6] ............................... A61L 2/04; A61L 11/00
[52] U.S. Cl. ................ 422/307; 241/23; 241/606; 264/311; 366/147; 494/13; 34/58
[58] Field of Search ............................. 422/307; 241/606, 241/23, 99; 264/311, 503, 309–312; 366/147, 146, 145; 494/13; 34/58, 594

[56] References Cited

U.S. PATENT DOCUMENTS

| | | | |
|---|---|---|---|
| 104,130 | 6/1870 | Eyster | 494/13 |
| 4,498,896 | 2/1985 | Leis | 494/13 |
| 5,185,126 | 2/1993 | Adamski et al. | 422/307 |
| 5,236,135 | 8/1993 | Wilson et al. | 241/21 |
| 5,282,319 | 2/1994 | Casquilho et al. | 34/58 |
| 5,470,146 | 11/1995 | Hawkins | 366/25 |

Primary Examiner—Krisanne Thornton
Assistant Examiner—Fariborz Moazzam
Attorney, Agent, or Firm—Thomas C. Saitta

[57] ABSTRACT

A syringe encapsulation device having a melt chamber heated by forced hot air to sufficient temperature to melt the plastic bodies of the syringes, where the melt chamber is coaxially mounted onto a rotating shaft and rotated when the plastic is in the molten state such that the molten plastic is centrifugally driven to the outer periphery of the melt chamber to safely encapsulate the needles once the molten plastic has hardened.

17 Claims, 4 Drawing Sheets

DEVICE FOR THE ENCAPSULATION OF PLASTIC SYRINGES

BACKGROUND OF THE INVENTION

This invention relates generally to the field of devices for the destruction, encapsulation or disposal of potentially hazardous plastic waste, especially such waste comprising used medical syringes with attached sharp needles or lancets, the needles or lancets being made of metal and having high melt temperatures. More particularly, the invention relates to such devices which melt and compact the plastic waste in a way to completely encapsulate the needles into a sterile, easily disposable slug. Even more particularly, the invention relates to such devices which accomplish the compaction or condensing of the molten plastic waste by centrifugal force.

It is necessary to dispose of used medical syringes, lancets and blood test strips in a manner which minimizes the possibility of injury or infection to persons handling the syringes, at the initial point of use and disposal as well as all along the handling chain to final disposition in a land fill or the like. Syringes, needles and other similar objects are well-known in medical situations for use in delivering treatment fluids into the bloodstream or for removing blood samples. There are numerous blood borne diseases, including HIV, TB, and Hepatitis B & C, which can be accidentally transferred from the carrier to another person coming into contact with the disease-laden blood. Unfortunately, medical personnel must routinely deal with potentially contaminated syringes and needles and are thereby often exposed to such diseases during the handling, storage and disposal of the used syringes and needles.

Numerous methods or devices have been developed to address this problem. Some such devices provide means to cap or enclose the needle, but enclosure of the needle by a physical housing requires the person to perform an additional physical act where inadvertent contact is possible and does not address the need to sterilize the syringes to kill infectious organisms. Devices are also known which provide protection from the syringe needles by melting the plastic portions of the syringes such that the needles are encased in the resulting plastic mass. This technique is an improvement over the capping method, since the used needle is simply deposited into the disposal device with minimal handling. The temperature achieved within the melt chambers of these devices is greater than that required to melt the plastic in order to also sterilize the waste material.

Examples of such combination disposal and sterilization devices are shown in U.S. Pat. No. 4,860,958 to Yerman and in U.S. Pat. No. 5,207,994 to Suzuki. These devices provide a cylindrical melting chamber with a reciprocating piston. The waste syringes are placed into the chamber, heated and compressed to form a puck or slug to encapsulate the needles. The plastic slug is then removed by opening separate access plates or doorways and disposed of. Both of these devices, as well as all other similar known devices, involve multiple joints, doorways, hinges and other components which are susceptible to fouling from plastic flash. Plastic flash is molten plastic which escapes from the melting chamber due to the effects of gravity or pressure from the compacting piston. Syringe plastic contains paraffin, which becomes a highly viscous liquid at temperatures well below those required to sterilize the plastic waste. The sterilization step requires temperatures in excess of 350 degrees F. to achieve sterilization in a relatively short time period. During the melting process, at about 275 degrees F., the paraffin becomes a highly viscous liquid which is forced past the seals and joints in the known devices. To counter this, highly efficient seals and joints must be constructed with very tight precision. These air and fluid tight seals prevent the escape of water vapor, steam and other outgas products produced during the melting process. Since they cannot escape and are non-compressible, they recondense on or within the waste slug and create gaps and voids within the slug through which the needle points may be exposed.

It is an object of this invention to provide a device for the destruction, sterilization and encapsulation of hazardous plastic waste products, and in particular waste such as used medical syringes with attached needles, lancets or the like which are made of metal, which provides a safe and efficient means to melt the plastic waste to form a disposable plastic slug with the needles securely encased therein by combination of pressure and temperature, where the pressure or force to compact the molten plastic waste is provided by centrifugal rotation of the melt chamber. It is a further object to provide such a device which eliminates the problems associated with plastic flash by eliminating the need for a compaction piston or ram.

SUMMARY OF THE INVENTION

The invention is a device for the safe, efficient and easy encapsulation of plastic waste material, and in particular bio-hazardous plastic waste material such as syringes or lancets having sharp needles made of metal. In general, the invention comprises a housing containing a motor means with a rotating shaft and melt chamber receiving means mounted onto the shaft, a forced hot air blower means capable of creating and directing air at elevated temperature into a melt chamber, such as a heat gun, and a removable melt chamber which receives the syringes. The melt chamber comprises a bottom, side wall and open top, preferably circular in horizontal cross-section, and is made of a suitable high temperature material such as glass or metal. A melt chamber closure member or lid removably mates with the open top of the melt chamber. The closure member comprises a nozzle aperture which allows passage of the hot air and preferably allows for insertion of a portion of the nozzle of the heat gun. The nozzle aperture is preferably sealed by a pair of closure flaps, hingedly mounted to the closure member such that the nozzle aperture is opened by the insertion of objects through the closure flaps. Control means for operation of the motor and heat gun are provided to automatically cycle the device.

The melt chamber and closure lid are kept external to the chamber and loaded with syringes, lancets and other hazardous plastic waste by insertion of the waste through the closure flaps on the lid. When the melt chamber is filled, it is placed into the melt chamber receiving means mounted on the motor shaft within the housing with the nozzle of the heat gun inserted a short distance into the nozzle aperture to open the closure flaps. The housing is closed and the operation cycle initiated. The heat gun delivers air into the melt chamber at a temperature sufficient to both melt the plastic and to sterilize any biological matter. When the plastic matter has melted, the heating element of the heat gun is deactivated and the motor rotates the melt chamber to develop centrifugal forces which drive the molten plastic radially outward to the side wall of the melt chamber, thereby encapsulating the metal needles such that no sharp points will be exposed after the molten plastic hardens. The rotation is stopped and the plastic allowed to cool, during which period a slug or puck of hardened plastic is formed. The melt chamber is then removed from the housing, the closure lid is removed and the puck is suitably disposed of by dumping it into a waste container without the need of direct handling, the puck having shrunk slightly during cooling such that it does not adhere to the bottom or side wall of the melt chamber.

DETAILED DESCRIPTION OF THE INVENTION

Figure 1:
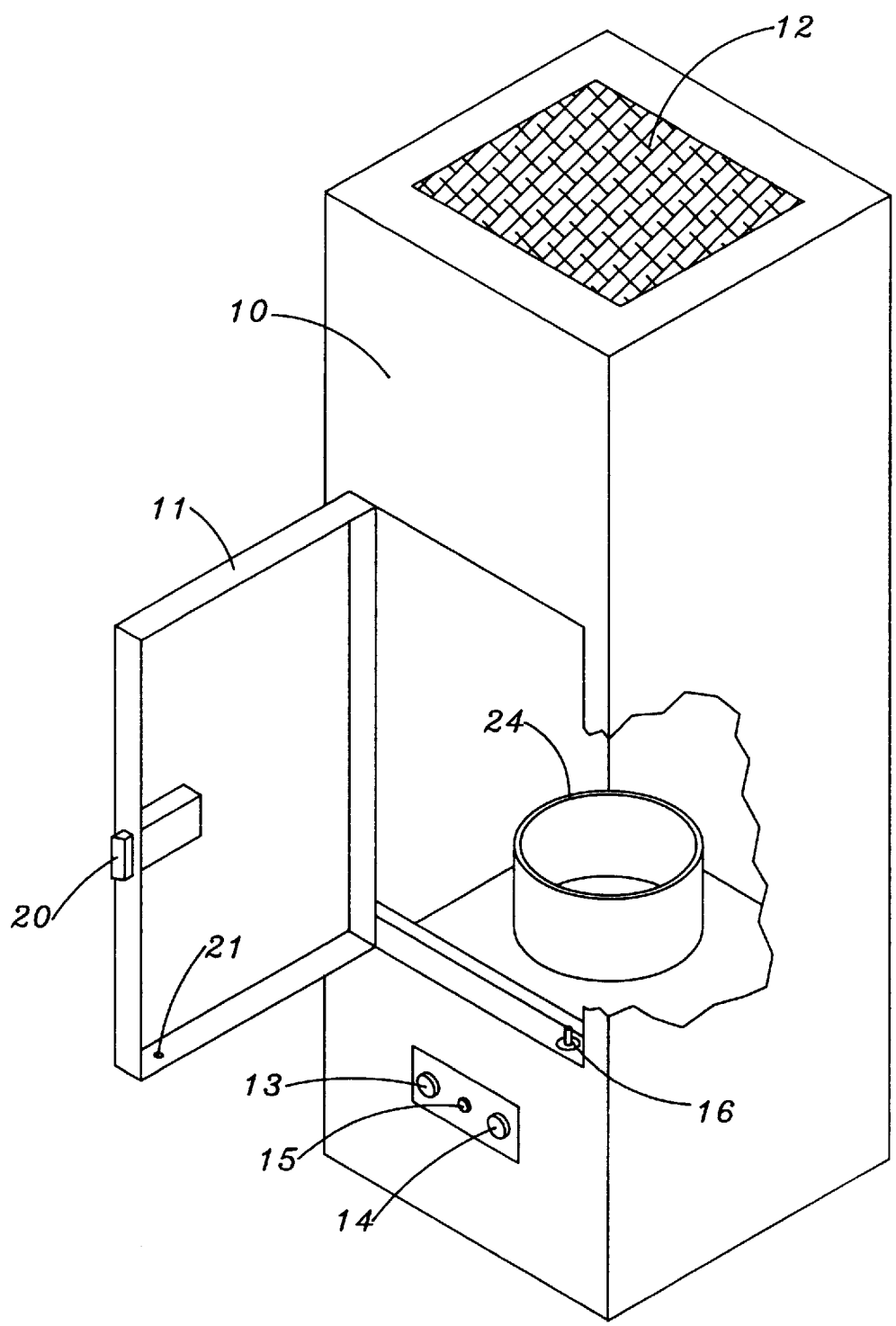
FIG. 1 is a perspective view of the device with the housing door open and the melt chamber removed.

With reference to the drawings, the invention will now be described in detail with regard for the best mode and the preferred embodiment. The invention is a device for the treatment of plastic waste, and in particular bio-hazardous waste, and for the encapsulation of hazardous plastic waste having sharp points or edges made of metal, such as in particular plastic-bodied syringes with metal needles. The invention both sterilizes the plastic waste and melts the plastic components of the waste to form a slug or puck which encapsulates the metal sharp points or edges in a safe manner when the molten plastic cools and hardens. Although not illustrated in the drawings, all electrical components are operationally connected in known manner to a power source and to each other.

Figure 3:
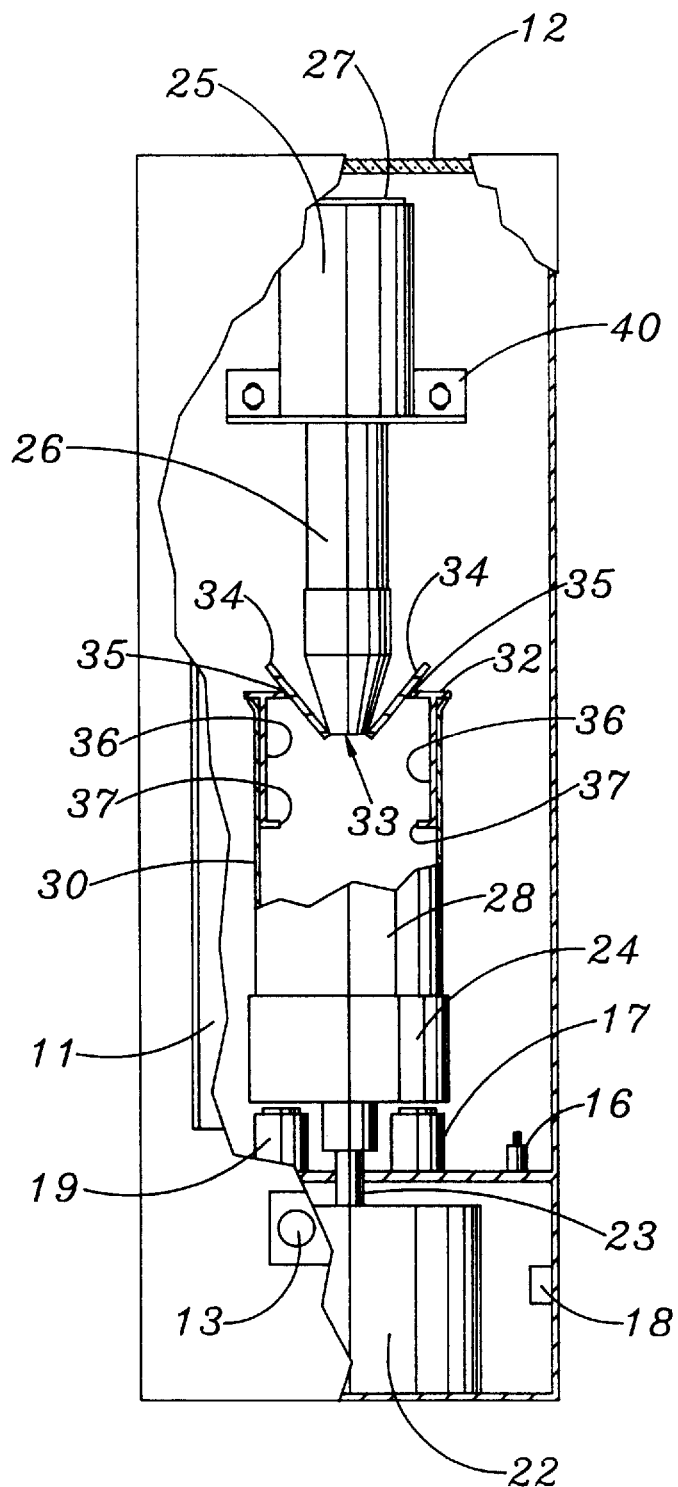
FIG. 3 is a view showing the melt chamber positioned within the housing, the housing and melt chamber shown in partial cross-section to expose certain components.

As shown best in FIGS. 1 and 3, the invention comprises in general a housing 10 formed of sheet metal, rigid plastic or other suitable material, having an access door 11 covering an opening into the interior of the housing 10. The door 11 has an exteriorly mounted handle 20 and lock pin receiving means 21. Door lock means 16, such as a solenoid reciprocating a pin or post, is mounted within the housing 10 and cooperates with lock pin receiving means 21 to secure or release door 11. The housing 10 as shown is rectangular, but other configurations are possible. Filter means 12, such as preferably a combination of particulate, activated charcoal and potassium permanganate filters, are provided to remove smoke particulates and other undesirable elements from air or gases passing out of housing 10. Actuation means 13, a switch to begin the processing operation, stop means 14, an emergency switch to stop the processing means, and operation indicator means 15, a light to indicate the processing operation is in progress, are attached to the exterior of the housing 10.

The base of housing 10 contains a motor 22 for rotating a shaft 23 which extends vertically within the interior of housing 10. Motor 22 may be any suitable type of motor capable of rotating shaft 23 between approximately 375 and 625 RPM, and most preferably at about 500 RPM for a melt chamber 28 having an inner diameter of approximately 3.5 inches. A melt chamber receiving means 24 is coaxially connected to the shaft 23, the melt chamber receiving means 24 preferably being a cup-like member, circular in horizontal cross-section, which is symmetrically configured to allow it to rotate in a balanced manner about the central vertical axis. Melt chamber receiving means 24 is preferably constructed of aluminum or other metal material to allow for relatively good heat transfer to the control thermostats. Deformable material, such elastomeric rings or buttons, may be positioned within the interior of the melt chamber receiving means 24 to better secure the melt chamber 28 therein. Melt spin controls means 17, preferably a high temperature thermostat, and automatic deactivation means 19, preferably a low temperature thermostat, are mounted beneath the melt chamber receiving means 24. Rotation control means 18, preferably a timer, is also positioned within the housing 10.

Mounted into the upper portion of the housing 10, by a mounting bracket 40 or other suitable means, is a forced hot air blower means 25, commonly referred to as a heat gun, having means to force air through and out the device and means to elevate the temperature of the air passing through. The heat gun 25 must be capable of delivering air heated sufficiently to sterilize and melt the plastic waste contained within the melt chamber 28, which means that preferably a temperature of between approximately 350 to 420 degrees F. is achieved in the melt chamber 28. Higher temperatures tend to burn the plastic and produce smoke, and lower temperatures will not suitably sterilize the bio-hazardous matter. It has been found that a heat gun 25 of 1200 watts operating at 115 volts with 45 to 55 cubic feet per minute of forced air which produces a temperature of approximately 1050 degrees F. at the nozzle 26 is suitable for this purpose. The heat gun 25 comprises an air intake member 27, preferably positioned adjacent the filter means 12 but with some separation distance, as shown in FIG. 3. The design allows the heat gun 25 to recycle most of the already heated air from within the housing 10 during the melt operation, such that the necessary high temperatures are quickly attained. The recycling effect also increases the efficiency of the filter means 12 in purifying the exhaust, since only a small amount of interior air will pass out through the filter means 12 at any given time. Nozzle 26 may be circular in cross-section or may be provided with diverter or focusing members to better direct the forced air in a desired pattern or direction. The nozzle 26 of heat gun 25 is aligned coaxially with the melt chamber receiving means 24.

Figure 2:
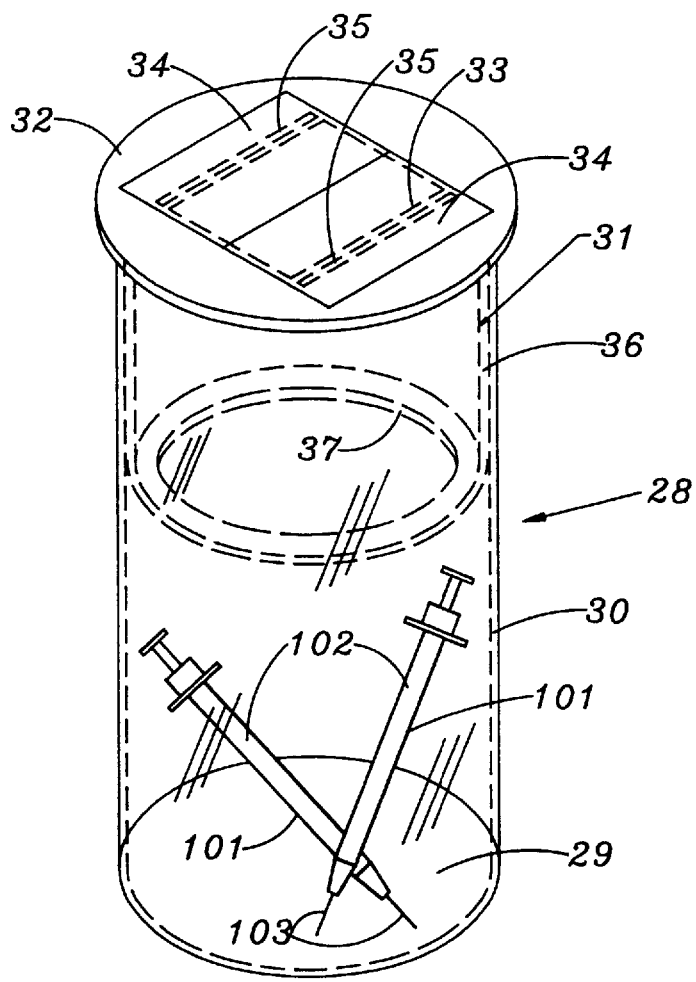
FIG. 2 is a perspective view of the melt chamber and closure lid.
Figure 4:
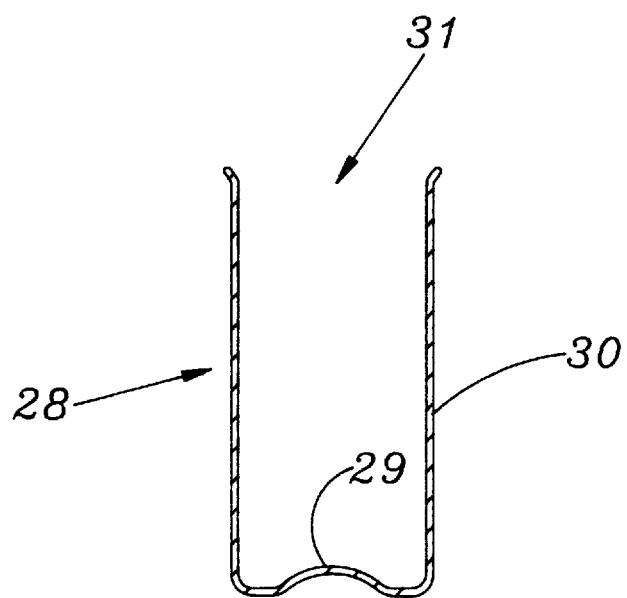
FIG. 4 shows an alternative embodiment for the melt chamber, where the bottom is raised in the center.

As seen in FIG. 2, melt chamber 28 is the container for receiving the syringes 101 having plastic bodies 102 and metal needles 103 for processing. Melt chamber 28 comprises a bottom 29 and side wall 30, preferably formed as a continuous body such that there are no seams or joints between the two components, with an open top 31. Melt chamber 28 is preferably circular in horizontal cross-section, as it needs to be symmetrically configured so as to rotate in a balanced manner, but other cross-sectional configurations such as hexagonal or octagonal can be utilized. Melt chamber 28 releasably mates with the melt chamber receiving means 24, such that the outer diameter of side wall 30 corresponds to the inner diameter of melt chamber receiving means 24, thus allowing the melt chamber 28 to be easily inserted into and removed from the melt chamber receiving means 24, with the two components contacting with sufficient friction such that the melt chamber 28 is rotated when motor 22 is activated. The bottom 29 of the melt chamber 28 may be flat, as shown in the majority of the figures, or raised at the central axis, as shown in FIG. 4, in a domed or conical manner. The provision of a raised bottom 29 may more efficiently direct the molten plastic to the outer periphery of the melt chamber 28 to better encapsulate the needles 103. Melt chamber may be composed of any suitable high temperature material, such as aluminum, stainless steel or other metals, preferably coated on the interior with Teflon or other similar low adhesion material, but it is most preferred that it be composed of an insulating high temperature material such as glass. Having an insulated melt chamber 28 decreases the melting time for the plastic waste syringes 101, since heat loss into the side wall 30 and bottom 29 are minimized. Utilizing a glass melt chamber also provides an easy way to ascertain when the melt chamber 28 is sufficiently full of syringes 101 to be processed.

The open top 31 of melt chamber 28 is sealed with a removable closure member or lid 32, preferably generally circular as shown in FIG. 2. The closure member 32 contains an axially located nozzle aperture 33, dimensioned sufficiently large to allow the end of nozzle 26 of heat gun 25 to pass through and into the interior of melt chamber 28. The closure member 32 releasably connects with melt chamber 28, preferably by an annular insertion sleeve member 36 which extends beneath the closure lid 32. The outer diameter of the sleeve member 36 corresponds to the inner diameter of the melt chamber 28, such that a relatively secure friction fit is obtained and whereby the closure member 32 will rotate along with the melt chamber 28. In a preferred embodiment, the bottom of the insertion sleeve member 36 comprises an annular lip or shoulder 37 which extends radially inward a short distance. This annular lip 37 prevents molten plastic from creeping up the side wall 30 of the melt chamber 28 and into the sleeve member 36 during the spin operation.

The nozzle aperture 33 is preferably covered by a pair of closure flaps 34, pivotally connected to opposing outer edges of the closure lid 32 by hinges 35, such that the closure flaps 34 may be pushed inward to provide access to the melt chamber 28. The flaps 34 remain horizontal to seal the nozzle aperture 33 in the passive position, maintained by spring biasing means or suitably designed with a center of gravity to the outside of each hinge 35 such that the weight of the flaps 34 themselves cause them to remain horizontal. The closure flaps 34 effectively seal the melt chamber 28 for safety purposes when it is removed from the housing 10 for insertion of syringes 101, yet allow the syringes 101 to be placed into the melt chamber 28 by pushing them through the closure flaps 34, which part to allow access to the melt chamber 28 but reclose when the syringe 101 has cleared the nozzle aperture 33. In the alternative, separate closure means which operate in manner similar to the closure flaps 34 could be provided which are removed from the melt chamber 28 prior to placing it into the housing 10 for processing. For example, a support stand or wall mounted bracket may be provided to hold the melt chamber 28 when it is out of the housing 10 for loading, and this bracket or stand could incorporate closure means which allow easy insertion of syringes 101 but provide a safety barrier against accidental contact.

When the melt chamber 28 has been loaded with a sufficient number of syringes 101 or similar hazardous plastic waste items, sufficient meaning that there are enough plastic bodies 102 to insure that there will be sufficient plastic to encapsulate the needles 103, the door 11 of the housing 10 is opened. The melt chamber 28 is inserted into the housing 10 by aligning the nozzle aperture 33 of the closure member 32 with the end of the nozzle 26 of the forced hot air blower means 25. The melt chamber 28 is angularly raised such that the nozzle 26 opens the closure flaps 34 and extends through the nozzle aperture into the melt chamber 28. In this manner the bottom 29 of the melt chamber clears the top of the melt chamber receiving means 24 and the melt chamber 28 can be coaxially aligned with the melt chamber receiving means 24, thereby allowing the melt chamber 28 to be inserted into the melt chamber receiving means 24. With the melt chamber 28 fully inserted, the end of the nozzle 26 remains extended through the nozzle aperture 33 of closure member 32, as shown in FIG. 3. The extension distance may be adjusted to control the separation of the two closure flaps 32 depending on whether a large or small opening is desired. The access door 11 is then closed, preferably closing a safety contact or switch to allow operation of the device.

Figure 5:
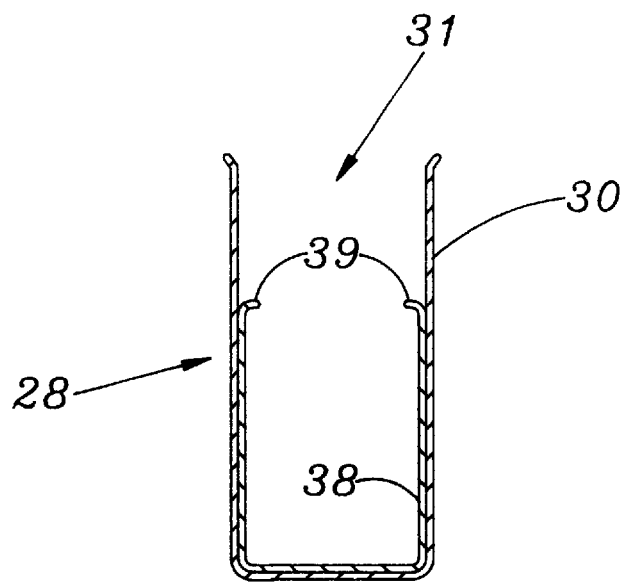
FIG. 5 shows an alternative embodiment for the invention, where a disposable insert container is positioned within the melt chamber.

The device is now activated through actuation means 13, such as by depressing a button or throwing a switch. This locks the door 11 in the closed position by activating the door lock means 16, such as by raising a locking pin into lock pin receiving means 21 mounted on the interior of door 11, activates the operation indicator means 15, and further initiates the forced hot air blower means 25 to deliver high temperature air into the melt chamber 28. The melting cycle can also be set up such that the heat gun 25 delivers high temperature air for an initial period to sterilize the biohazardous material and begin the melting process, followed by a final period of somewhat reduced temperature to continue the melt process while precluding burning of the plastic waste. The sterilizing and melting operation using components as set forth above typically requires 3 to 4 minutes, and may be controlled with a timer, but it is preferred that melt spin control means 17 be a thermostat set to respond at a particular temperature. In this manner variables such as changes in the ambient temperature or the actual temperature of the device itself can be accounted for to insure that the melt is properly accomplished. As shown in FIG. 3, a thermostat 17 is positioned adjacent the bottom of the melt chamber receiving means 24. Even with a melt chamber 28 composed of a good insulating material there is still some heat transfer, and the thermostat 17 is set to respond at the external temperature of approximately 140 degrees F., which corresponds to a temperature within the melt chamber 28 of between 350 and 420 degrees F. with the components as described. Upon sensing this temperature, which is sufficient to melt and sterilize the plastic waste, the melt spin control means 17 turns off the heating means within the heat gun 25 but allows the forced air means to continue, and initiates the spin operation by activating the motor 22. The melt chamber 28 is rotated at preferably approximately 500 RPM for about 10 seconds, controlled by rotation control means 18, preferably a timer, thereby creating a sufficient amount of centrifugal force to drive the molten plastic to the side wall 30 adjacent the bottom 29 to adequately encapsulate the needles 103 of the syringes 101. The annular lip 37 on the insertion sleeve member 36 prevents excessive creep of the molten plastic up the side wall 30. Alternatively, as shown in FIG. 5, a disposable insert container 38 which matingly corresponds to the interior of melt chamber 28 and composed preferably of a plastic having a melting point above 420 degrees F., also having an insert lip 39 to prevent excess creep, may be utilized.

After the spin operation is completed, the rotation control means 18 turns off the motor 22 and the cooling cycle begins. The forced air means of the heat gun 25 continues to deliver non-warmed air into the melt chamber 28 to reduce the required cooling time. Deactivation means 19, which may be a timer but is preferably a thermostat set at approximately 110 degrees F. for the components as described, deactivates the blower means, turns off the operation indicator means, and retracts the door lock means 16 when the temperature within the melt chamber 28 has lowered below both the melting point of the plastic waste, thus insuring that the puck or slug will have hardened, and when the melt chamber 28 is sufficiently cool to handle. Because plastic shrinks when cooling, the puck will have retracted from the side wall 30 and bottom 29 of the melt chamber 28, such that when the door 11 is opened, the melt chamber 28 is removed from the housing 10 and the closure member 32 is removed from the melt chamber 28, the solid waste puck with the needles 103 safely encapsulated can be poured into a proper waste disposal container without need for direct handling.

It is contemplated that equivalents and substitutions for certain components and elements set out above may be obvious to those skilled in the art. The true scope and definition of the invention therefore is to be as set forth in the following claims.

I claim:

1. A device for the encapsulation of plastic syringes using centrifugal force, the device comprising a removable, rotatable melt chamber to receive plastic syringes, a housing to receive said melt chamber, forced hot air blower means comprising means to heat air and means to deliver air into said melt chamber to elevate the temperature within said melt chamber to a temperature sufficient to melt said plastic syringes, and motor means to rotate said melt chamber after said syringes are melted to distribute said melted syringes by centrifugal force.

2. The device of claim 1, where said melt chamber is circular in cross-section.

3. The device of claim 1, where said melt chamber is composed of glass.

4. The device of claim 1, where said motor means further comprises a melt chamber receiving means to releasably retain said melt chamber.

5. The device of claim 1, where said forced hot air blower means comprises a nozzle and where said melt chamber comprises a bottom, side wall, open top, and a removable closure member having a nozzle aperture to receive said nozzle.

6. The device of claim 5, where said closure member comprises a pair of hinged closure flaps covering said nozzle aperture, said closure flaps opening inwardly to receive said nozzle.

7. The device of claim 5, where said closure member further comprises an annular insertion member which extends beneath said closure member and abuts said side wall of said melt chamber.

8. The device of claim 1, further comprising actuation means to activate said forced hot air blower means to elevate the temperature within said melt chamber, melt spin control means to deactivate said means to heat said air and to initiate said motor means to rotate said melt chamber, rotation control means to deactivate said motor means to stop said rotation, and deactivation means to deactivate said means to deliver air into said melt chamber.

9. The device of claim 8, where said actuation means comprises a switch.

10. The device of claim 8, where said melt spin control means comprises a thermostat.

11. The device of claim 8, where said rotation control means comprises a timer.

12. The device of claim 8, where said deactivation means comprises a thermostat.

13. The device of claim 1, further comprising a disposable insert container positioned within said melt chamber to receive said syringes.

14. The device of claim 1, where said motor means rotates said melt chamber between approximately 375 and 625 RPM.

15. The device of claim 1, where said forced hot air blower means elevates said temperature within said melt chamber to between approximately 350 to 420 degrees F.

16. A method for the encapsulation of plastic syringes comprising the steps of:

(A) providing a device comprising a rotatable melt chamber to receive plastic syringes, forced hot air blower means comprising means to heat air and means to deliver air into said melt chamber to elevate the temperature within said melt chamber to a temperature sufficient to melt said plastic syringes, and motor means to rotate said melt chamber;

(B) inserting said plastic syringes into said melt chamber;

(C) delivering forced hot air into said melt chamber to elevate the temperature within said melt chamber to a temperature sufficient to melt said plastic syringes;

(D) rotating said melt chamber to distribute said melted plastic syringes by centrifugal force; and (E) allowing said melted plastic syringes to harden.

17. The method of claim 16, where said step of delivering hot air into said melt chamber is discontinued prior to rotating said melt chamber.

* * * * *